US008855691B2

(12) United States Patent
Kamiya et al.

(10) Patent No.: US 8,855,691 B2
(45) Date of Patent: Oct. 7, 2014

(54) RADIOGRAPHIC IMAGING DEVICE AND COMMUNICATION MODE SETTING DEVICE

(75) Inventors: Takeshi Kamiya, Kanagawa (JP); Yusuke Kitagawa, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 223 days.

(21) Appl. No.: 13/347,332

(22) Filed: Jan. 10, 2012

(65) Prior Publication Data

US 2012/0208576 A1  Aug. 16, 2012

(30) Foreign Application Priority Data

Feb. 15, 2011 (JP) ................................. 2011-030093

(51) Int. Cl.
G05B 19/18 (2006.01)
G05B 23/00 (2006.01)
A61B 6/00 (2006.01)

(52) U.S. Cl.
CPC .............. *A61B 6/4283* (2013.01); *A61B 6/4233* (2013.01); *A61B 6/566* (2013.01); *A61B 6/4423* (2013.01); *A61B 6/4291* (2013.01); *A61B 6/4411* (2013.01)
USPC ................. 455/500; 700/66; 700/56; 700/60; 700/61; 700/65; 340/2.1; 340/5.2

(58) Field of Classification Search
USPC .................................... 700/66, 56, 60, 61, 65
See application file for complete search history.

(56) References Cited

U.S. PATENT DOCUMENTS

| 7,664,557 | B2 * | 2/2010 | Danzer et al. .................... 700/66 |
| 7,684,536 | B2 * | 3/2010 | Kudo .................................. 378/8 |
| 2005/0246120 | A1 | 11/2005 | Hein et al. | |
| 2006/0255904 | A1 * | 11/2006 | Danzer et al. .................. 340/5.2 |
| 2010/0245931 | A1 | 9/2010 | Sato | |
| 2012/0206233 | A1 * | 8/2012 | Kamiya et al. ................. 340/2.1 |

FOREIGN PATENT DOCUMENTS

| JP | 2003-334185 A | 11/2003 |
| JP | 2006-296676 A | 11/2006 |
| JP | 2010-239449 A | 10/2010 |
| WO | WO2005/076810 A2 | 8/2005 |

OTHER PUBLICATIONS

Notification of Reasons for Rejection issued by the Japanese Patent Office on Nov. 5, 2013 in Japanese Patent Application No. 2011-030093.

* cited by examiner

*Primary Examiner* — Bobbak Safaipour
(74) *Attorney, Agent, or Firm* — Jean C. Edwards, Esq.; Edwards Neils PLLC

(57) ABSTRACT

A radiographic imaging device has: a generating unit that generates image data expressing a radiographic image formed by irradiated radiation; a first communicating unit at which wireless communication is possible selectively in either of a direct communication mode or an indirect communication mode; a storing unit that stores a setting of a communication mode; and a control unit that, if a setting to carry out communication in the direct communication mode has been made, controls the first communicating unit to carry out wireless communication in the direct communication mode, and, if a setting to carry out communication in the indirect communication mode has been made, controls the first communicating unit to attempt wireless communication in the indirect communication mode with a control device that controls the radiographic imaging device, and, if communication is impossible, controls the first communicating unit to carry out wireless communication in the direct communication mode.

6 Claims, 12 Drawing Sheets

FIG.8

| CONSOLE ID | IMAGE CAPTURING ENVIRONMENT | COMMUNICATION MODE | IP ADDRESS | SUBNET MASK | ... | SSID | ENCRYPTION KEY | ... |
|---|---|---|---|---|---|---|---|---|
| A | IMAGING ROOM A | INFRASTRUCTURE MODE | 192. ... | 255. ... | ... | SATSUEIA | XXXXX | ... |
| B | IMAGING ROOM B | INFRASTRUCTURE MODE | 192. ... | 255. ... | ... | SATSUEIB | XXXXX | ... |
| C | MEDICAL ROUNDS | INFRASTRUCTURE MODE | 192. ... | 255. ... | ... | KAISHIN | XXXXX | ... |
| D | PATIENT'S HOME | AD HOC MODE | 192. ... | 255. ... | ... | KAISHIN | XXXXX | ... |

110

RADIOGRAPHIC IMAGING DEVICE AND COMMUNICATION MODE SETTING DEVICE

CROSS-REFERENCE TO RELATED APPLICATIONS

This application claims priority under 35 USC 119 from Japanese Patent Application No. 2011-030093 filed on Feb. 15, 2011, the disclosure of which is incorporated by reference herein.

BACKGROUND OF THE INVENTION

1. Field of the Invention

The present invention relates to a radiographic imaging device and a communication mode setting device. In particular, the present invention relates to a radiographic imaging device in which wireless communication is possible selectively either in a direct communication mode, in which devices directly communicate with one another, or in an indirect communication mode, in which devices communicate with one another via another wireless device, and that carries out capturing of a radiographic image expressed by radiation that has been emitted from a radiation source and transmitted through a subject, and the present invention relates to a communication mode setting device that sets the communication mode of the radiographic imaging device.

2. Description of the Related Art

FPDs (Flat Panel Detectors) have been put into practice in recent years. In an FPD, a radiation sensitive layer is disposed on a TFT (Thin Film Transistor) active matrix substrate, and the FPD detects irradiated radiation such as X-rays, γ-rays, α-rays or the like, and directly converts the radiation into data of a radiographic image that expresses the distribution of the irradiated radiation amount, and outputs the data. Portable radiographic imaging devices (hereinafter also called electronic cassettes) also have been put into practice. The portable radiographic imaging device incorporates therein a panel-type radiation detector such as an FPD or the like, electronic circuits including an image memory, and a power source section, and stores, in the image memory, the radiographic image data outputted from the radiation detector. As compared with radiographic imaging devices that utilize conventional X-ray films or imaging plates, a radiographic imaging device that uses the radiation detector has the advantages that images can be confirmed immediately, and through imaging (video imaging), that caries out capturing of radiographic images continuously, can also be carried out.

Various types of such radiation detectors have been proposed. For example, there are: an indirect-conversion-type radiation detector that once converts radiation into light at a scintillator of CsI:Tl, GOS ($Gd_2O_2S$:Tb) or the like, and converts the converted light into charges at sensor portions such as photodiodes or the like, and accumulates the charges; a direct-conversion-type radiation detector that converts radiation into charges at a semiconductor layer of amorphous selenium or the like; and the like. In the radiographic imaging device, the charges accumulated in the radiation detector are read-out as electric signals, the read-out electric signals are amplified at amplifiers, and thereafter, are converted into digital data at an A/D (analog/digital) converting section.

Because the electronic cassette has excellent portability, images of a subject can be captured while the subject lies as is on a stretcher or a bed, and further, it is also easy to adjust the region to be captured by changing the position of the radiation detecting panel. Therefore, even situations in which images of a subject who cannot move are to be captured can be dealt with flexibly, and further, the electronic cassette can also be used in capturing radiographic images at the home of a patient or the like.

Japanese Patent Application Laid-Open (JP-A) No. 2006-296676 discloses an X-ray device for medical rounds that carries out capturing of radiographic images by using a medical rounds cart equipped with a radiation generating device.

The electronic cassette carries out transmission and reception of various types of control information and image data with a control device such as a console or the like that controls the capturing of radiographic images. However, connecting the electronic cassette to the console by a communication cable and making the communication between the electronic cassette and the console be wired communication leads to a deterioration in the ability to handle the electronic cassette.

Thus, it is desirable to utilize a structure in which, by providing the electronic cassette and the console with the function of carrying out wireless communication, the communication cable that connects the electronic cassette and the console is omitted, and the transfer of image data from the electronic cassette to the console, and the transmission and reception of various types of control information between the electronic cassette and the console, are carried out by wireless communication.

In general wireless communication such as wireless communication carried out via a wireless LAN, devices communicate with one another via a wireless base station such as a wireless LAN access point or the like. However, in a case in which the electronic cassette is brought to and used at a patient's room, a disaster site, the home of a patient, or the like, the state of communication is not always good, and therefore, there are cases in which communication with the console cannot be carried out via a wireless base station.

SUMMARY OF THE INVENTION

The present invention provides a radiographic imaging device and a communication mode setting device.

In accordance with a first aspect of the present invention, there is provided a radiographic imaging device which includes: a generating unit that generates image data expressing a radiographic image formed by irradiated radiation; a first communicating unit at which wireless communication is possible selectively in either of a direct communication mode, in which devices communicate directly with one another, or an indirect communication mode, in which devices communicate with one another via another wireless device; a storing unit that stores a setting as to which of the direct communication mode or the indirect communication mode wireless communication is to be carried out in; and a control unit that, in a case in which a setting to carry out communication in the direct communication mode has been made at the storing unit, controls the first communicating unit to carry out wireless communication in the direct communication mode, and, in a case in which a setting to carry out communication in the indirect communication mode has been made at the storing unit, controls the first communicating unit to attempt wireless communication in the indirect communication mode with a control device that controls the radiographic imaging device, and, if communication is impossible, controls the first communicating unit to carry out wireless communication in the direct communication mode.

In accordance with a second aspect of the present invention, in the first aspect, the first communicating unit may receive, from an external device, switching instruction information that instructs switching of a communication mode, and the control unit may control the first communicating unit to carry out wireless communication in the communication mode expressed by the switching instruction information received at the first communicating unit.

In accordance with a third aspect of the present invention, there is provided a communication mode setting device which includes: a second communicating unit at which wireless communication with the radiographic imaging device of the second aspect is possible; a specifying unit that, in accordance with predetermined conditions, specifies a communication mode in which the radiographic imaging device is to carry out communication with a control device that is an object of communication; and a control unit that controls the second communicating unit to transmit, to the radiographic imaging device, switching instruction information that instructs switching to the communication mode specified by the specifying unit.

BRIEF DESCRIPTION OF THE DRAWINGS

A preferred embodiment of the present invention will be described in detail based on the following figures, wherein:

FIG. 8 is a schematic drawing showing an example of the data structure of communication setting information relating to the exemplary embodiment;

DETAILED DESCRIPTION OF THE INVENTION

Hereinafter, forms for implementing the present invention will be described in detail with reference to the drawings. Note that, here, description is given of an example of a case in which the present invention is applied to a radiographic imaging system that carries out capturing of radiographic images by using an electronic cassette.

First, the structure of an electronic cassette 12 relating to the present exemplary embodiment is described with reference to FIG. 1.

Figure 1:
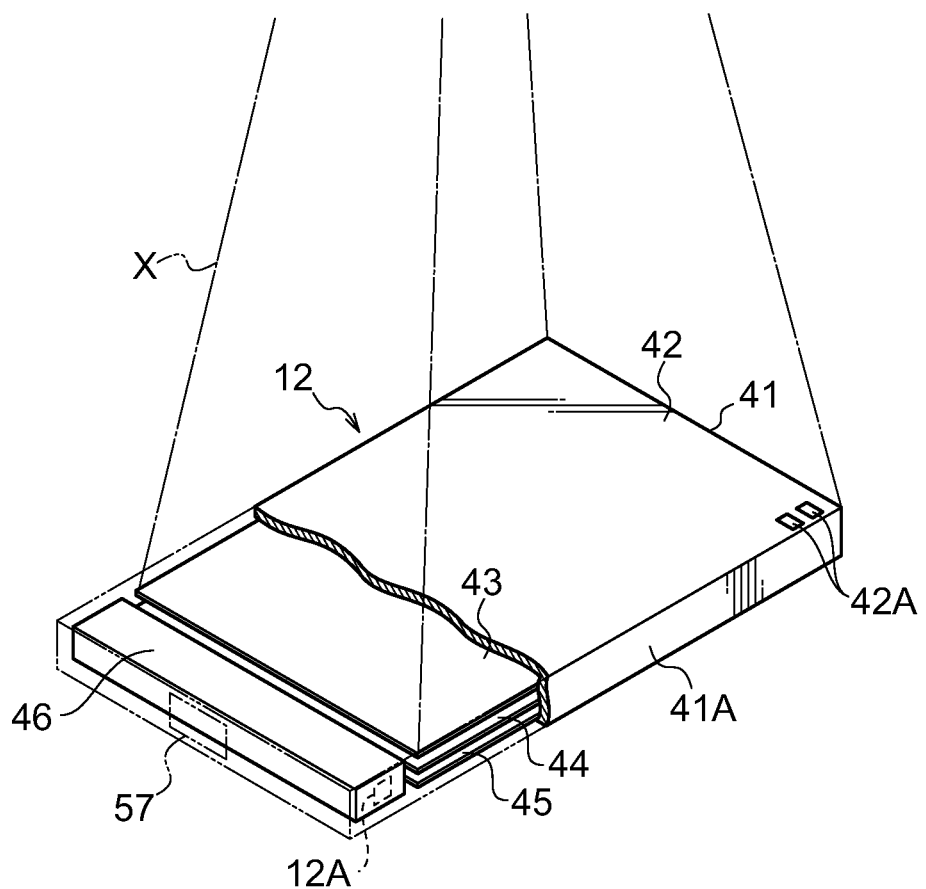
FIG. 1 is a transparent perspective view showing the structure of an electronic cassette relating to an exemplary embodiment.

As shown in FIG. 1, the electronic cassette 12 has a housing 41 formed from a material through which radiation X is transmitted, and is a structure that is waterproof and airtight. In a case in which the electronic cassette 12 is used in an operating room or the like, there is the concern that blood or other various germs will adhere thereto. Thus, by making the electronic cassette 12 be a waterproof and airtight structure and disinfectingly cleaning it as needed, the one electronic cassette 12 can be used repeatedly in continuation.

A grid 43, a radiation detector 44, and a lead plate 45 are disposed within the housing 41 in that order from an irradiated surface 42 side of the housing 41 on which the radiation X is irradiated. The grid 43 removes scattered radiation that arises at the time when the radiation X passes through a subject. The radiation detector 44 detects the radiation X that has passed through the subject. The lead plate 45 absorbs the back-scattered radiation of the radiation X. Note that the irradiated surface 42 of the housing 41 may be structured as the grid 43.

A display portion 42A, that is formed from plural LEDs and is for displaying the operating state of the electronic cassette 12, is provided at the irradiated surface 42 of the housing 41. Note that the display portion 42A may be structured by light-emitting elements other than LEDs, or may be structured by a display means such as a liquid crystal display, an organic EL display, or the like. Further, the display portion 42A may be provided at a region other than the irradiated surface 42.

A case 46, that accommodates electronic circuits including microcomputers and accommodates a secondary battery that is chargeable, is disposed at one end side of the interior of the housing 41. The radiation detector 44 and the electronic circuits are operated by electric power that is supplied from the secondary battery disposed in the case 46. In order to avoid damage, that accompanies irradiation of the radiation X, to the various types of circuits that are accommodated within the case 46, it is desirable to place a lead plate or the like at the irradiated surface 42 side of the case 46. Note that the electronic cassette 12 relating to the present exemplary embodiment is a parallelepiped at which the shape of the irradiated surface 42 is rectangular, and the case 46 is disposed at one end portion in the longitudinal direction thereof.

An operation panel 57 having various types of buttons is provided at the side surface of the housing 41.

Owing to the portability of the electronic cassette 12 relating to the present exemplary embodiment, the electronic cassette 12 can be used, not only in a radiographic imaging room within a hospital, but also in a form of capturing radiographic images during medical rounds in a hospital, a form of capturing radiographic images in the house of a patient, a form of capturing radiographic images at a disaster site, or the like.

Figure 2:
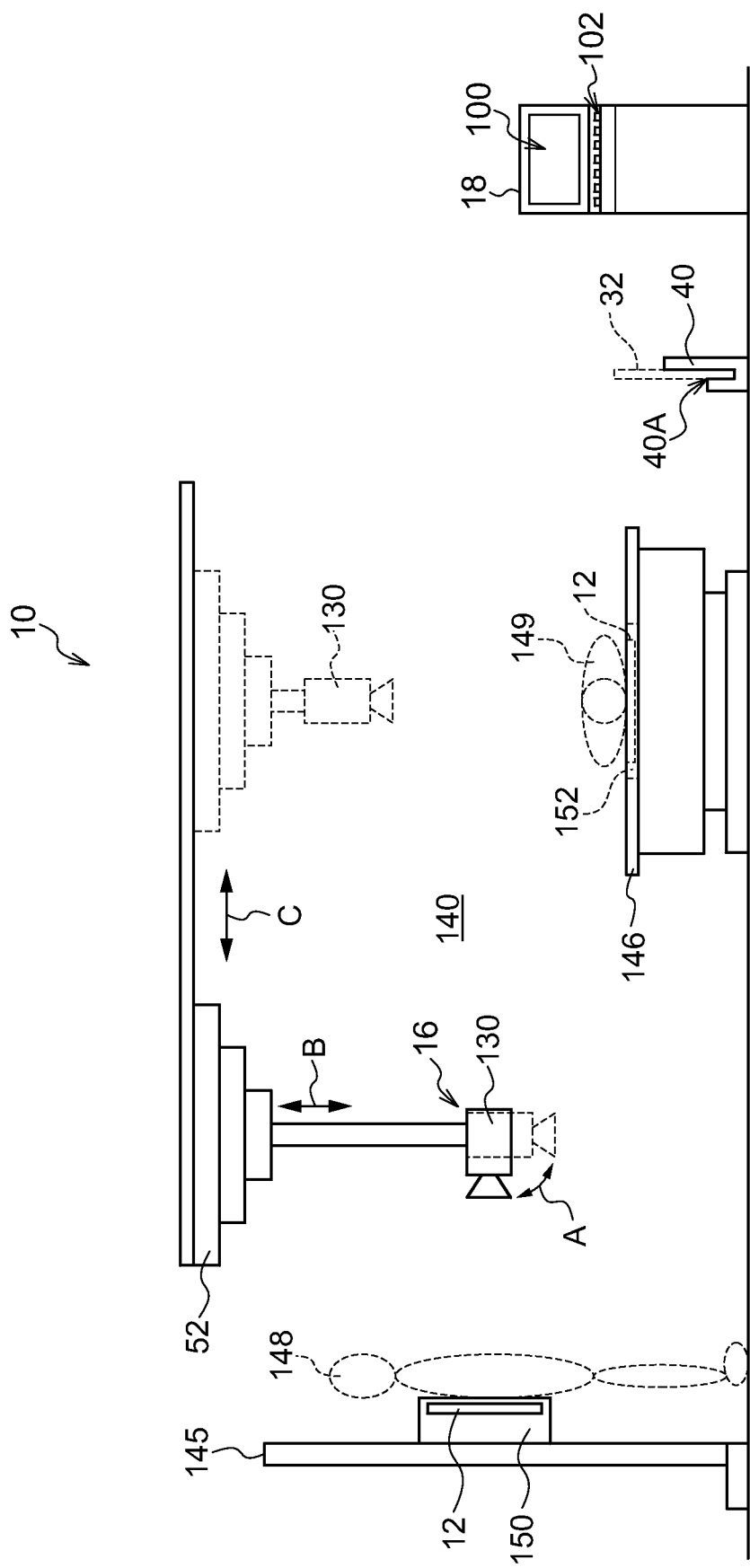
FIG. 2 is a side view showing an example of the state of arrangement of respective devices, in a radiographic imaging room, of a radiographic imaging system relating to the exemplary embodiment.

FIG. 2 shows an example of the arranged state of respective devices, in a radiographic imaging room 140, of an imaging system 10 that carries out capturing of radiographic images by using the electronic cassette 12 relating to the present exemplary embodiment.

The imaging system 10 includes: a radiation generating device 16 that irradiates, from a radiation source 130 and onto a subject, the radiation X of a radiation amount according to exposure conditions; the electronic cassette 12 that captures a radiographic image formed by the irradiated radiation X; a cradle 40 that charges the battery that is incorporated in the electronic cassette 12; and a console 18 that controls the electronic cassette 12 and the radiation generating device 16.

A standing position stand 145, that is used when carrying out radiographic imaging in a standing position, and a supine position stand 146, that is used when carrying out radiographic imaging in a supine position, are set in the radiographic imaging room 140. The space in front of the standing position stand 145 is an imaging position 148 for the subject when radiographic imaging in the standing position is carried out. The space above the supine position stand 146 is an imaging position 149 for the subject when radiographic imaging in the supine position is carried out.

A holding portion 150 that holds the electronic cassette 12 is provided at the standing position stand 145. The electronic cassette 12 is held at the holding portion 150 when capturing of a radiographic image is carried out in the standing position. Similarly, a holding portion 152 that holds the electronic cassette 12 is provided at the supine position stand 146. The electronic cassette 12 is held at the holding portion 152 when capturing of a radiographic image is carried out in the supine position.

Further, a supporting/moving mechanism 52, that supports the radiation source 130 such that the radiation source 130 is rotatable around a horizontal axis (the direction of arrow A in FIG. 2), is movable in the vertical direction (the direction of arrow B in FIG. 2), and is movable in the horizontal direction (the direction of arrow C in FIG. 2), is provided in the radiographic imaging room 140 in order to make both radiographic imaging in the standing position and radiographic imaging in the supine position possible by radiation from the single radiation source 130. Here, the supporting/moving mechanism 52 respectively has a driving source that rotates the radiation source 130 around the horizontal axis, a driving source that moves the radiation source 130 in the vertical direction, and a driving source that moves the radiation source 130 in the horizontal direction (none of these driving sources is illustrated).

On the other hand, an accommodating portion 40A, in which the electronic cassette 12 can be stored, is formed in the cradle 40.

At times of non-use, the battery incorporated in the electronic cassette 12 is charged in a state in which the electronic cassette 12 is stored in the accommodating portion 40A of the cradle 40. At times of capturing radiographic images, the electronic cassette 12 is taken-out from the cradle 40 by an operator, and is held at the holding portion 150 of the standing position stand 145 if the imaging posture is standing, or is held at the holding portion 152 of the supine position stand 146 if the imaging posture is supine.

Here, at the imaging system 10 relating to the present exemplary embodiment, the radiation generating device 16 and the console 18 are respectively connected by a cable, and transmission and receipt of various types of information therebetween is carried out by wired communication. However, the cable that connects the radiation generating device 16 and the console 18 is omitted from FIG. 2. Further, transmission and receipt of various types of information between the electronic cassette 12 and the console 18 is carried out by wireless communication. Note that the communication between the radiation generating device 16 and the console 18 as well may be carried out by wireless communication.

Figure 3:
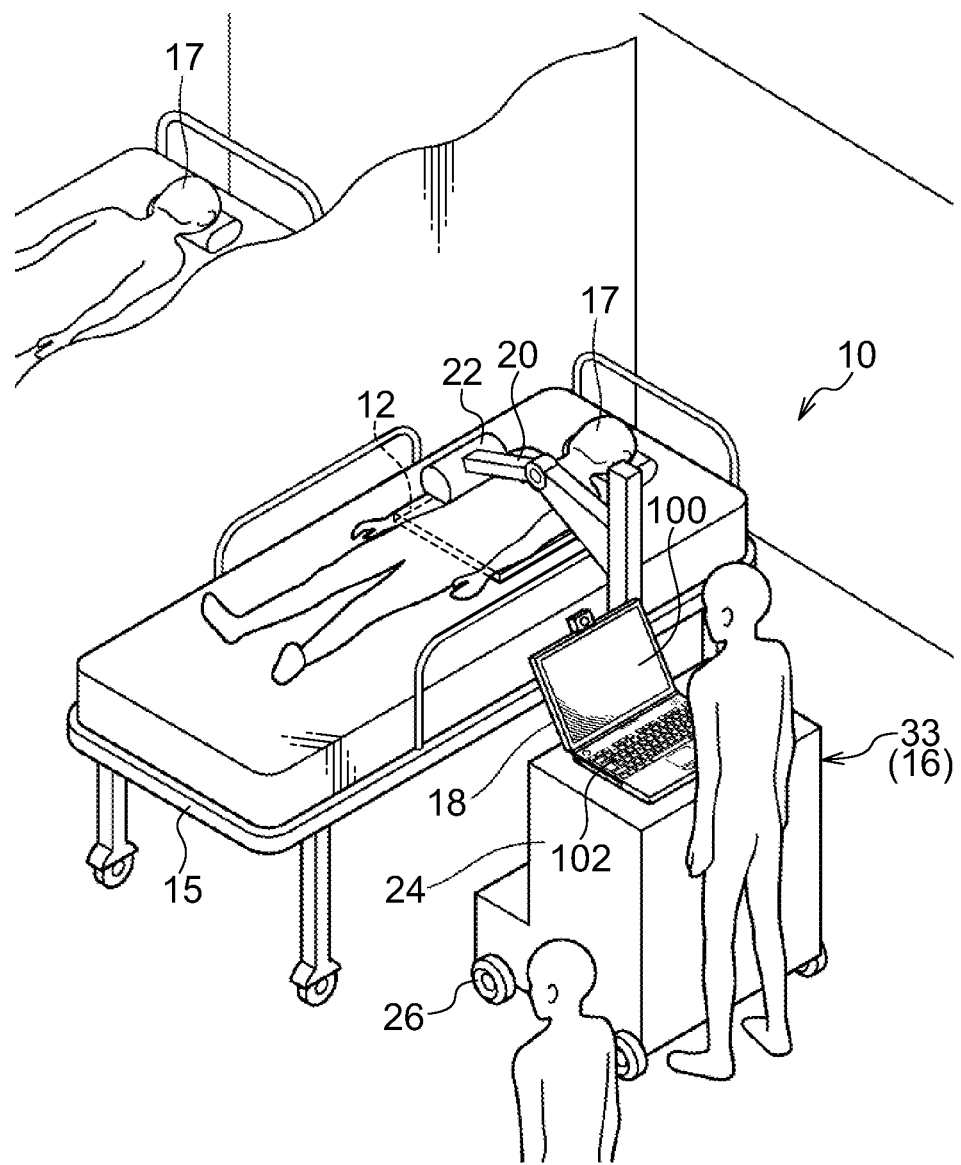
FIG. 3 is a perspective view showing a state in which the radiographic imaging system relating to the exemplary embodiment is disposed in a patient's room.

An example of the arranged state of the imaging system 10, that carries out capturing of radiographic images in a patient's room by using the electronic cassette 12 relating to the present exemplary embodiment, is shown in FIG. 3.

The radiation generating device 16 is structured as a medical rounds cart 33 so that it can be moved within the hospital. The medical rounds cart 33 has an arm 20. A radiation emitting section 22, that incorporates the radiation source 130 therein, is provided at one end portion of the arm 20. Further, wheels 26 are provided at the bottom portion of a main body portion 24 of the radiation generating device 16, and the radiation generating device 16 can be moved within the hospital.

The console 18 shown in FIG. 3 is structured by a personal computer, such as a notebook-type personal computer or the like, and receives, from the operator, various types of operational inputs relating to image capturing, such as the exposure conditions and the like.

Further, the radiation emitting section 22 is disposed above a patient 17 who is lying supine on a bed 15. When capturing of a radiographic image is instructed via the console 18, the radiation generating device 16 irradiates, from the radiation emitting section 22, radiation of a radiation amount that corresponds to the aforementioned exposure conditions or the like. By passing through the patient 17, the radiation emitted from the radiation generating device 16 carries image information, and thereafter, is irradiated onto the electronic cassette 12.

Figure 4:
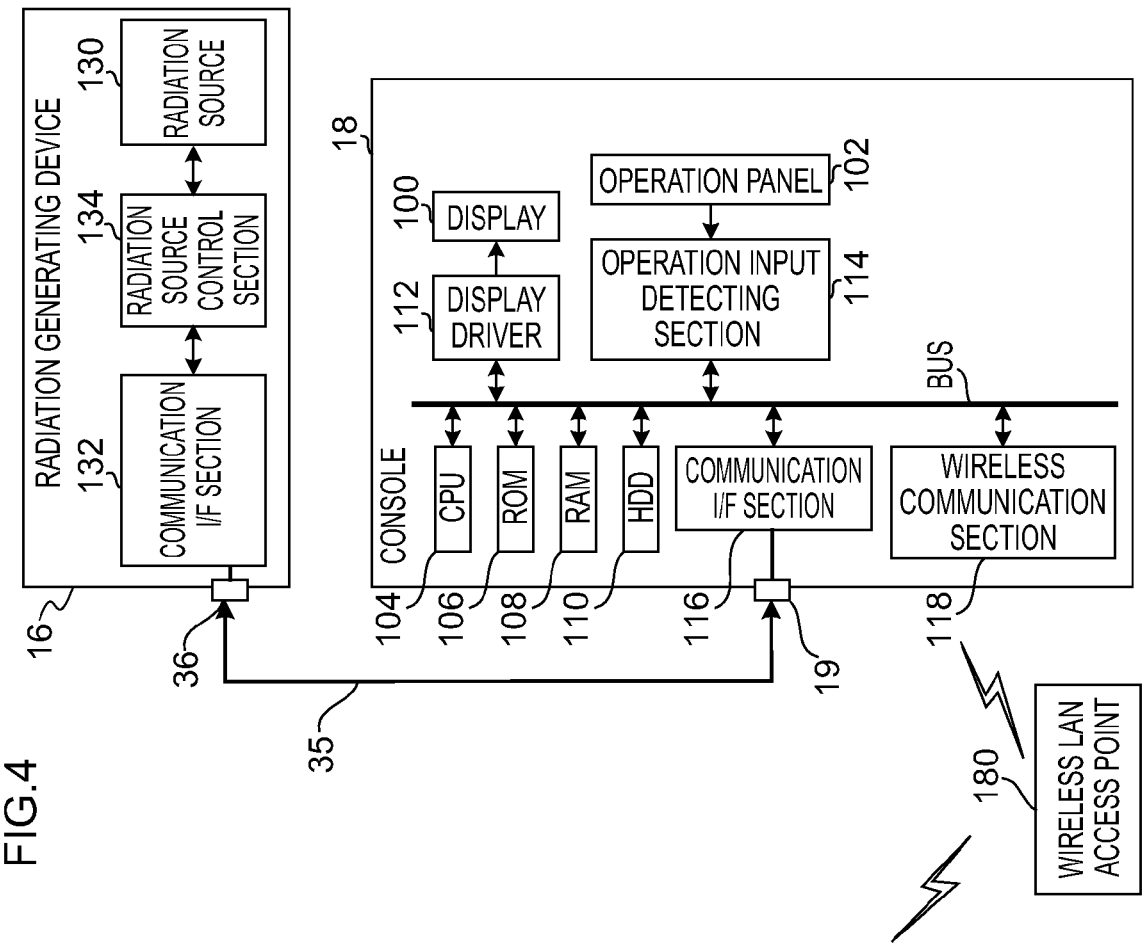
FIG. 4 is a block diagram showing the structure of main portions of the electrical system of the imaging system relating to the exemplary embodiment.
Figure 4:
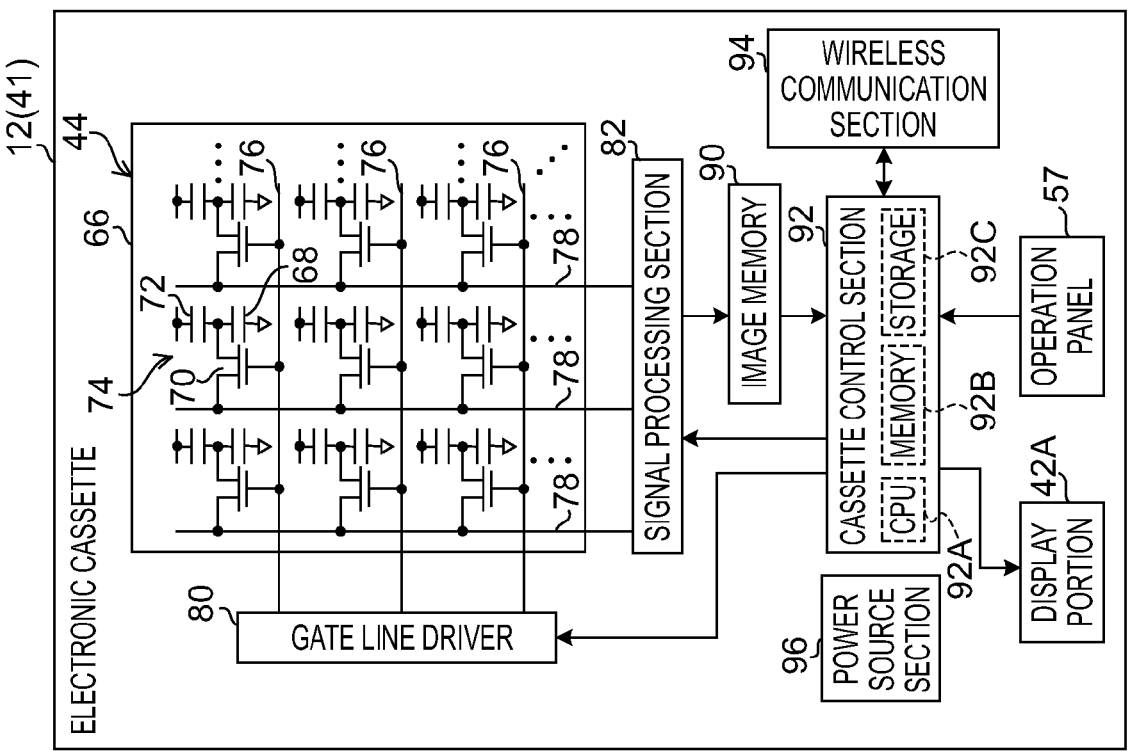

The structure of main portions of the electrical system of the radiographic imaging system 10 relating to the present exemplary embodiment is described next with reference to FIG. 4.

A connection terminal 36 for carrying out communication with the console 18 is provided at the radiation generating device 16. A connection terminal 19 for carrying out communication with the radiation generating device 16 is provided at the console 18. The connection terminal 36 of the radiation generating device 16 and the connection terminal 19 of the console 18 are connected by a cable 35.

The radiation detector 44 incorporated within the electronic cassette 12 is structured by a photoelectric conversion layer, that absorbs the radiation X and converts the radiation X into charges, being layered on a TFT active matrix substrate 66. The photoelectric conversion layer is formed from, for example, amorphous a-Se (amorphous selenium) whose main component is selenium (e.g., a content of greater than or equal to 50%). When the radiation X is irradiated, the photoelectric conversion layer converts the irradiated radiation X into charges by generating, at the interior thereof, charges (pairs of electrons and holes) of a charge amount corresponding to the irradiated radiation amount. Note that, instead of a radiation-charge conversion material that directly converts the radiation X into charges such as amorphous selenium, the radiation detector 44 may convert the radiation X into charges indirectly by using a phosphor material and photoelectric conversion elements (photodiodes). Gadolinium oxysulfide (GOS) and cesium iodide (CsI) are well known as phosphor materials. In this case, conversion from the radiation X into light is carried out by the phosphor material, and conversion from light into charges is carried out by the photodiodes that are the photoelectric conversion elements.

Numerous pixel portions 74 having storage capacitors 68, that accumulate the charges generated at the photoelectric conversion layer, and TFTs 70, that are for reading-out the charges accumulated in the storage capacitors 68, are arranged in the form of a matrix on the TFT active matrix substrate 66. (In FIG. 4, the photoelectric conversion layer corresponding to the individual pixel portions 74 is shown schematically as sensor portions 72.) The charges, that are generated at the photoelectric conversion layer accompanying the irradiation of the radiation X onto the electronic cassette 12, are accumulated in the storage capacitors 68 of the individual pixel portions 74. Due thereto, the image information, that is carried by the radiation X irradiated on the electronic cassette 12, is converted into charge information and is held at the radiation detector 44.

Plural gate lines 76, that extend in a given direction (the row direction) and are for turning the TFTs 70 of the individual pixel portions 74 on and off, and plural data lines 78, that extend in a direction (the column direction) orthogonal to the gate lines 76 and are for reading-out the accumulated charges from the storage capacitors 68 via the TFTs 70 that have been turned on, are provided at the TFT active matrix substrate 66. The individual gate lines 76 are connected to a gate line driver 80, and the individual data lines 78 are connected to a signal processing section 82. When charges are accumulated in the storage capacitors 68 of the individual pixel portions 74, the TFTs 70 of the individual pixel portions 74 are turned on in order in units of rows by signals supplied from the gate line driver 80 via the gate lines 76. The charges, that are accumulated in the storage capacitors 68 of the pixel portions 74 whose TFTs 70 have been turned on, are transferred through the data lines 78 as analog electrical signals and are inputted to the signal processing section 82. Accordingly, the charges, that are accumulated in the storage capacitors 68 of the individual pixel portions 74, are read-out in order in units of rows.

Although not illustrated, the signal processing section 82 is equipped with an amplifier and a sample hold circuit that are provided for each of the individual data lines 78. The charge signals that are transferred through the individual data lines 78 are amplified at the amplifiers, and thereafter, are held in the sample hold circuits. A multiplexer and an A/D (analog/digital) converter are connected in that order to the output sides of the sample hold circuits. The charge signals, that are held in the individual sample hold circuits, are inputted in order (serially) to the multiplexer, and are converted into digital image data by the A/D converter.

An image memory 90 is connected to the signal processing section 82. The image data outputted from the A/D converter of the signal processing section 82 is stored in order in the image memory 90. The image memory 90 has a storage capacity that can store image data of an amount of a predetermined number of images. Each time capturing of a radiographic image is carried out, the image data obtained by the capturing are successively stored in the image memory 90.

The image memory 90 is connected to a cassette control section 92 that controls the overall operation of the electronic cassette 12. The cassette control section 92 is structured by a microcomputer, and has a CPU (Central Processing Unit) 92A, a memory 92B including a ROM (Read Only Memory) and a RAM (Random Access Memory), and a nonvolatile storage 92C formed by a HDD (Hard Disk Drive), a flash memory, or the like.

A wireless communication section 94 is connected to the cassette control section 92.

Figure 5A:
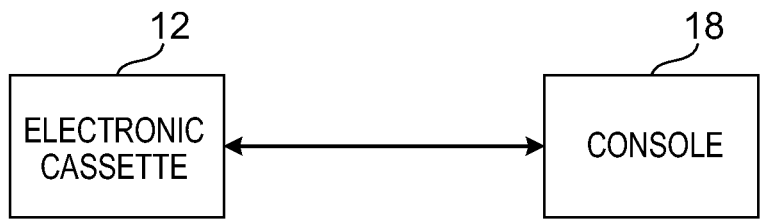
FIG. 5A is a block diagram showing an ad hoc mode.
Figure 5B:
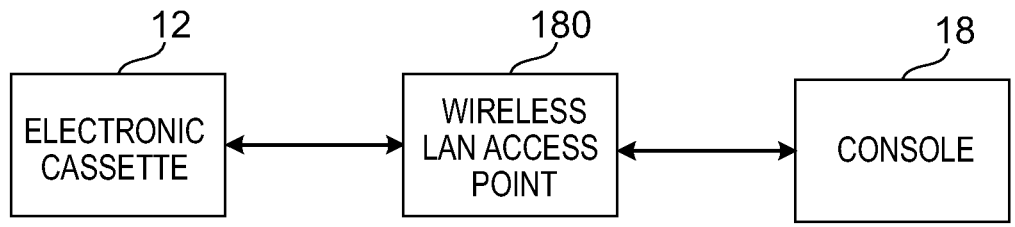
FIG. 5B is a block diagram showing an infrastructure mode.

The wireless communication section 94 corresponds to wireless LAN (Local Area Network) standards such as IEEE (Institute of Electrical and Electronics Engineers) 802.11a/b/g or the like, and controls the transfer of various types of information to and from external devices by wireless communication. As communication modes for carrying out communication with external devices, the wireless communication section 94 has an ad hoc mode (direct communication mode) in which devices directly communicate with one another as shown in FIG. 5A, and an infrastructure mode (indirect communication mode) in which devices communicate with one another via a wireless LAN access point 180 as shown in FIG. 5B. Wireless communication is possible by selectively switching the communication mode to the ad hoc mode or the infrastructure mode.

The cassette control section 92 controls settings relating to the network such as the communication mode at the time of carrying out communication at the wireless communication section 94, the IP address (Internet Protocol Address), the subnet mask, the default gateway, the IP address of the DNS (Domain Name System) server, and the like, and settings relating to wireless communication such as the SSID (Service Set Identifier) and encryption key and the like. Via the wireless communication section 94, the cassette control section 92 can carry out wireless communication in the set communication mode with the console 18 that belongs to the set network, and can transmit and receive various types of information to and from the console 18. The cassette control section 92 stores exposure conditions, that are described hereafter and that are received from the console 18 via the wireless communication section 94, and starts reading-out of charges on the basis of the exposure conditions.

A display portion 42A is connected to the cassette control section 92, and the cassette control section 92 can control the state of the display of the display portion 42A.

Further, an operation panel 57 is connected to the cassette control section 92, and the cassette control section 92 can grasp the contents of operations with respect to the operation panel 57.

A power source section 96 is provided at the electronic cassette 10. The above-described various types of circuits and respective elements (microcomputers and the like that function as the display portion 42A, the operation panel 57, the gate line driver 80, the signal processing section 82, the image memory 90, the wireless communication section 94, and the cassette control section 92), are operated by electric power supplied from the power source section 96. The power source section 96 incorporates therein the aforementioned battery (secondary battery) so that the portability of the electronic cassette 12 is not impaired, and supplies electric power from the charged battery to the various types of circuits and respective elements. Note that, in FIG. 4, illustration of the wires that connect the power source section 96 with the various types of circuits and respective elements is omitted.

On the other hand, the console 18 has a display 100 that displays an operation menu, captured radiographic images and the like, and an operation panel 102 that is structured to include plural keys and at which various types of information and operating instructions are inputted.

The console 18 relating to the present exemplary embodiment includes a CPU 104 that governs the operations of the overall device, a ROM 106 in which various types of programs, including control programs, and the like are stored in advance, a RAM 108 that temporarily stores various types of data, an HDD 110 that stores and holds various types of data, a display driver 112 that controls the display of various types of information on the display 100, and an operation input detecting section 114 that detects the operated state of the operation panel 102. Further, the console 18 has a communication I/F section 116 that is connected to the connection terminal 19 and that, via the connection terminal 19 and the cable 35, carries out transmission and reception of various types of information, such as exposure conditions that will be described later and the like, with the radiation generating device 16, and a wireless communication section 118 that carries out transmission and reception of various types of information, such as exposure conditions and the like, with the electronic cassette 12 by wireless communication.

The wireless communication section 118 also has, as communication modes, an ad hoc mode in which devices communicate directly with one another, and an infrastructure mode in which devices communicate with one another via the wireless LAN access point 180. Wireless communication is possible in the ad hoc mode and the infrastructure mode.

The CPU 104, the ROM 106, the RAM 108, the HDD 110, the display driver 112, the operation input detecting section 114, the communication I/F section 116, and the wireless communication section 118 are connected to one another via a system bus BUS. Accordingly, the CPU 104 can access the ROM 106, the RAM 108 and the HDD 110, and can respectively carry out control of display of various types of information on the display 100 via the display driver 112, control of transmission and reception of various types of information with the radiation generating device 16 via the communication I/F section 116, and control of transmission and reception of various types of information with the electronic cassette 12 via the wireless communication section 118. Further, the CPU 104 can, via the operation input detecting section 114, grasp the operated state of the operation panel 102 by a user.

On the other hand, the radiation generating device 16 has the radiation source 130 that emits the radiation X, a communication I/F section 132 that transmits and receives various types of information such as exposure conditions and the like to and from the console 18, and a radiation source control section 134 that controls the radiation source 130 on the basis of received exposure conditions.

The radiation source control section 134 also is realized by a microcomputer, and the communication I/F section 132 and the radiation source 130 are respectively connected thereto. The radiation source control section 134 carries out control relating to the radiation emitting operations of the radiation source 130.

Operation of the radiographic imaging system 10 relating to the present exemplary embodiment is described next.

Figure 6:
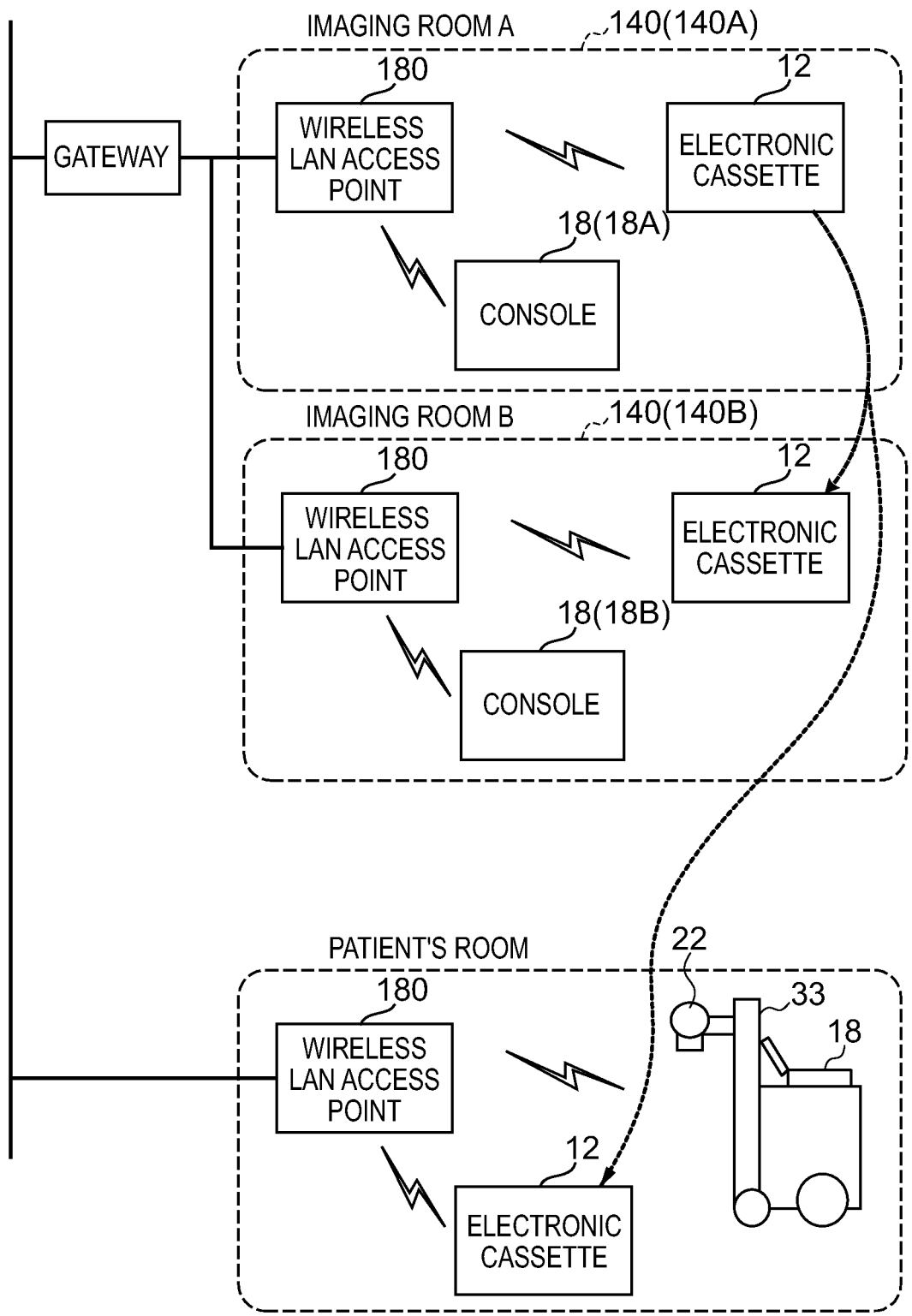
FIG. 6 is a block diagram showing the structure of the radiographic imaging systems in radiographic imaging rooms and in a patient's room.
Figure 7:
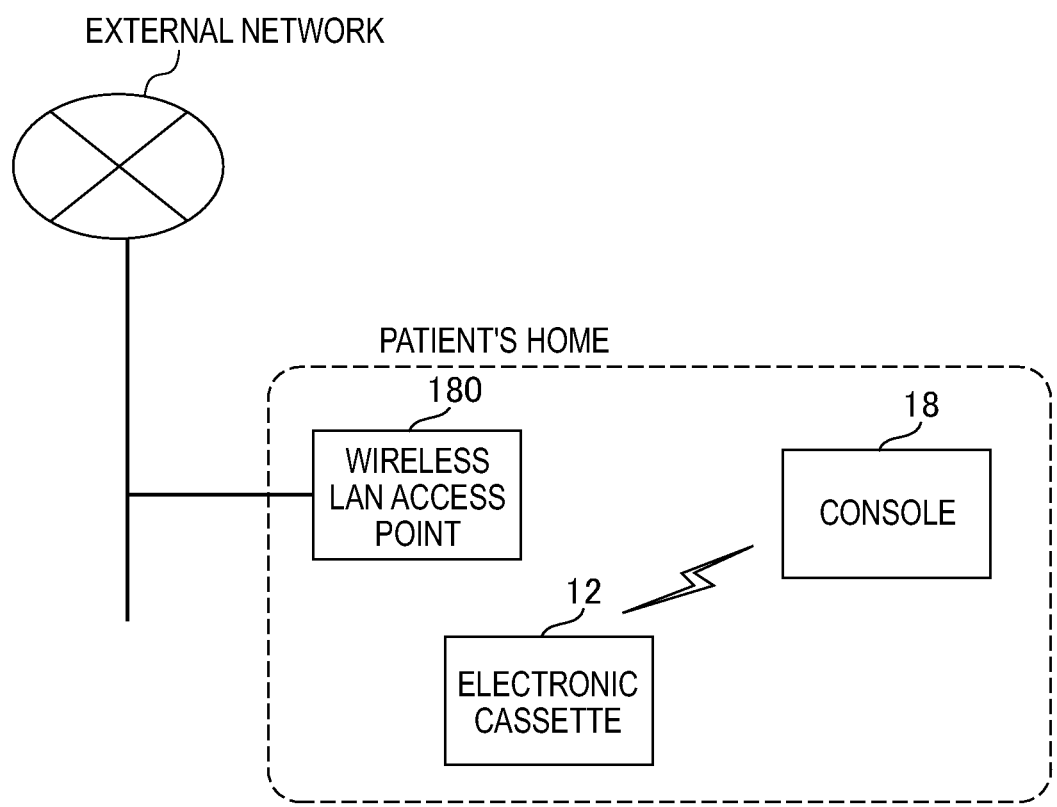
FIG. 7 is a block diagram showing the structure of the radiographic imaging system at the home of a patient.

By changing the settings relating to the network and the settings relating to wireless communication and switching the console 18 with which communication is possible, the electronic cassette 12 relating to the present exemplary embodiment can be used in the capturing of radiographic images in the radiographic imaging room 140 within a hospital or the capturing of radiographic images within a hospital together with the medical rounds cart 33 that has the radiation generating device 16 as shown in FIG. 6, or can be used in the capturing of radiographic images at a patient's home together with the portable radiation generating device 16 as shown in FIG. 7.

In wireless communication, it is difficult to grasp the device that is to be the partner in communication. Therefore, there are cases in which the electronic cassette 12 carries out communication with the console 18 that is different than the console 18 that was originally intended to be the object of communication.

For example, as shown in FIG. 6, in a case in which the consoles 18 (18A, 18B) are provided in the two radiographic imaging rooms 140 (140A, 140B) respectively and settings have been carried out such that the electronic cassette 12 communicates with the console 18A of the radiographic imaging room 140A, the electronic cassette 12 carries out communication with the console 18A even if the electronic cassette 12 is moved to the radiographic imaging room 140B. Further, for example, even if the electronic cassette 12, at which settings have been carried out such that the electronic cassette 12 communicates with the console 18A, is brought to a patient's room and an attempt is made to carry out radiographic image capturing together with the medical rounds cart 33, the electronic cassette 12 carries out communication with the console 18A.

In order to check for mistakes in the image capturing, the operator causes the radiographic images that were captured by the electronic cassette 12 to be displayed on the display 100 of the console 18 and confirms the images. However, if the communication settings have not been set correctly, there are cases in which the radiographic images are displayed on the display 100 of the console 18 that exists in a completely different location.

Further, if capturing of radiographic images is carried out at a patient's home as shown in FIG. 7, in a case in which the electronic cassette 12 is to carry out communication in the infrastructure mode, there are cases in which the electronic cassette 12 is connected to the wireless LAN access point 180 of the home of the patient 17.

Thus, the console 18 relating to the present exemplary embodiment stores, in the HDD 110, communication setting information such as the settings relating to the network, the settings relating to wireless communication, the IP address of the console 18 that is the partner in communication, and the like for each of the consoles 18.

An example of the data structure of the communication setting information that is stored in the HDD 110 is shown in FIG. 8.

A console ID for identifying the console 18, environment information that expresses the image capturing environment, settings relating to the network, settings relating to wireless communication, the IP address of the console 18 that is the partner in communication, and the like for each of the consoles 18 are stored as communication setting information.

If the console 18 that is the partner in communication of the electronic cassette 12 is to be changed, such as in a case in which the electronic cassette 12 is used in another radiographic imaging room 140, or is used in a patient's room together with the medical rounds cart 33, or is used in the home of a patient, or the like, the operator operates the operation panel 102 at the console 18 that can communicate with the electronic cassette 12, and carries out the operation of changing the partner in communication.

Figure 9:
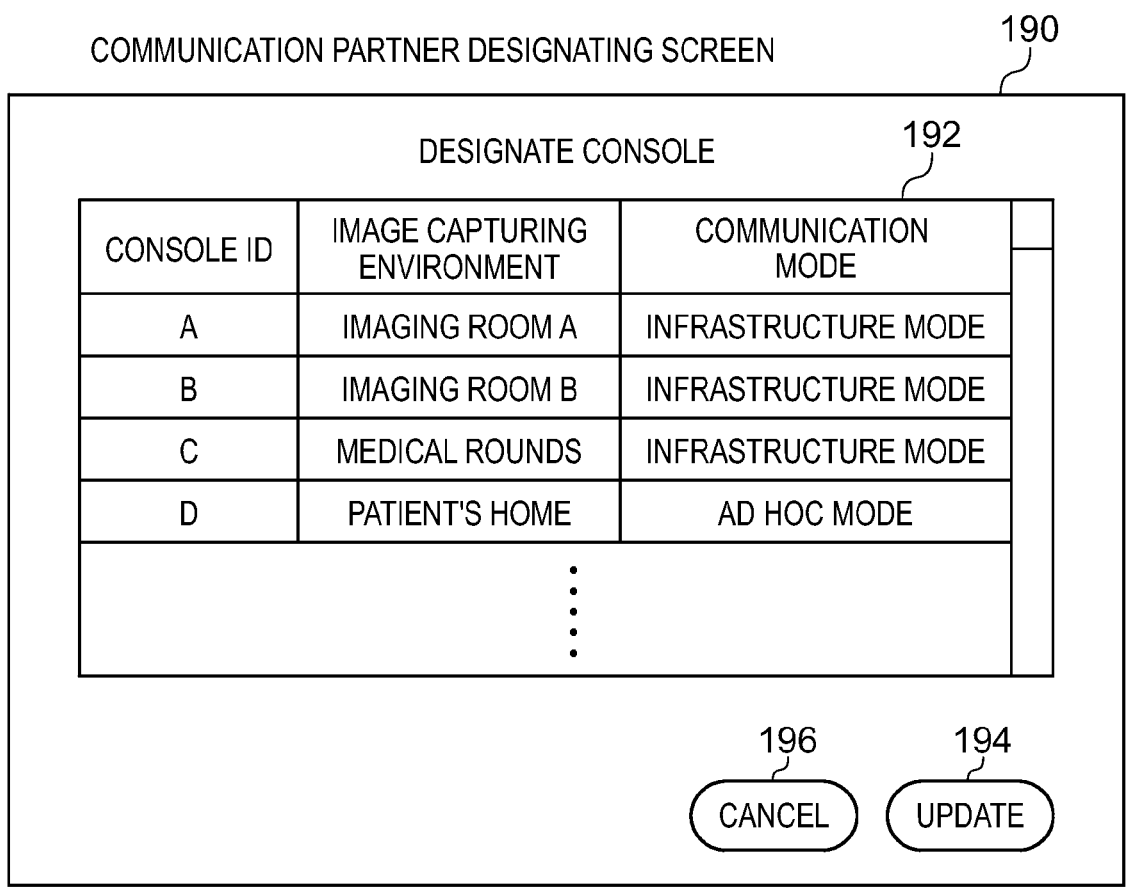
FIG. 9 is a schematic drawing showing the structure of a communication partner designating screen relating to the exemplary embodiment.

A structural drawing showing an example of the structure of a communication partner designating screen 190, that is displayed on the display 100 at the time of carrying out the operation of changing the partner in communication at the console 18, is shown in FIG. 9.

On the basis of the communication setting information stored in the HDD 110, the console ID, the image capturing environment, and the communication mode for each of the consoles 18 are displayed in a list display portion 192 of the communication partner designating screen 190.

From the list display portion 192 of the communication partner designating screen 190, the operator designates the row of the console 18 that is to be the object of communication. Due thereto, the designated row is reverse-displayed in the list display portion 192. In a case in which the operator carries out updating of the console 18 that is to be the partner in communication, the operator designates an update button 194. In a case in which the operator cancels the updating, the operator designates a cancel button 196.

At the console 18, when the update button 194 of the communication partner designating screen 190 is designated, switching instruction information transmitting processing that transmits, to the electronic cassette 12, switching instruction information that instructs switching of the console 18 that is the object of communication, is executed.

Figure 10:
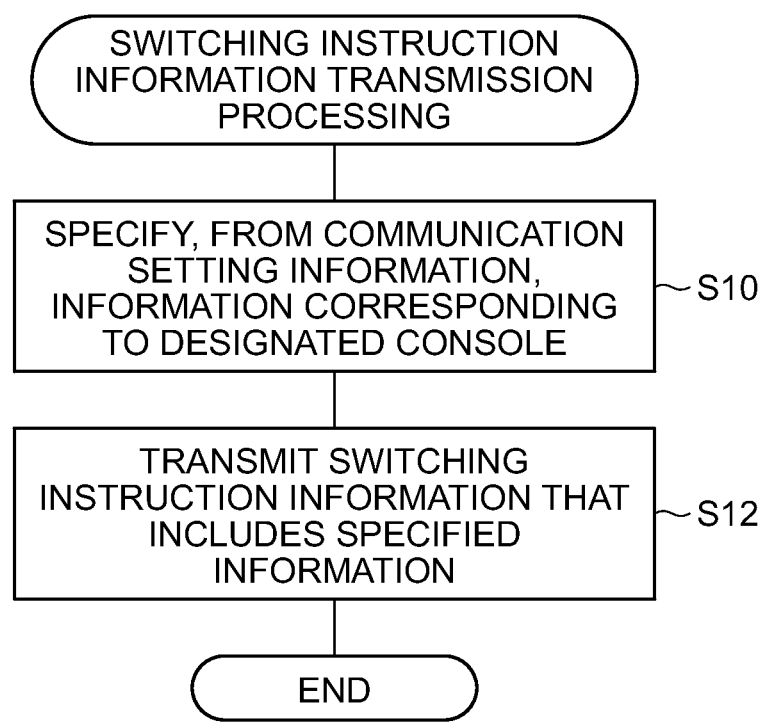
FIG. 10 is a flowchart showing the flow of switching instruction information transmitting processing relating to the exemplary embodiment.

A flowchart showing the flow of the switching instruction information transmitting processing that is executed by the CPU 104 of the console 18 relating to the present exemplary embodiment, is shown in FIG. 10.

In step S10 of FIG. 10, information relating to the settings relating to the network and the settings relating to wireless communication of the designated console 18 is specified from the communication setting information stored in the HDD 110.

In next step S12, switching instruction information, that includes the information relating to the settings relating to the network and the settings relating to wireless communication that were specified in above-described step S10, and that instructs switching of the console 18 that is the object of communication, is transmitted to the electronic cassette 12, and processing ends.

At the electronic cassette 12, when the switching instruction information is received, updating processing that updates the settings relating to the network is executed.

Figure 11:
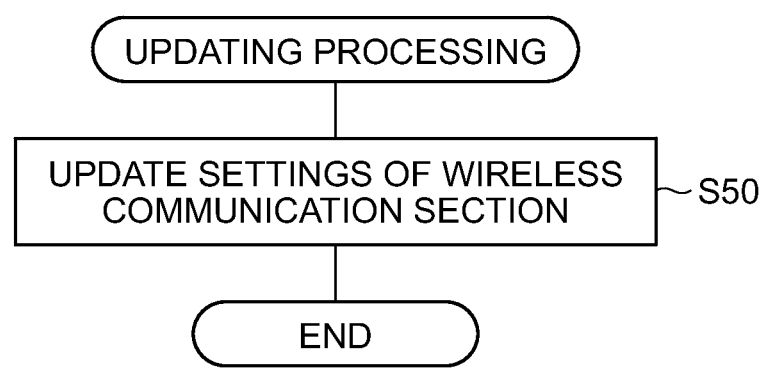
FIG. 11 is a flowchart showing the flow of updating processing relating to the exemplary embodiment.

A flowchart showing the flow of the updating processing that is executed by the CPU 92A of the cassette control section 92 relating to the present exemplary embodiment is shown in FIG. 11.

In step S50 of FIG. 11, the settings relating to the network and the settings relating to wireless communication of the wireless communication section 94 are updated in accordance with the settings relating to the network and the settings relating to wireless communication that are included in the received object of communication updating instruction information, and processing ends. Note that, in a case in which the electronic cassette 12 must be restarted in order to make the updated settings valid, restarting may be carried out at the time of the end of processing in the updating processing.

Due thereto, after updating, the electronic cassette 12 can communicate with the console 18 that was designated in the communication partner designating screen 190.

In a case in which the infrastructure mode is set as the communication mode of the electronic cassette 12, communication is carried out via the wireless LAN access point 180. However, there are cases in which, if the state of communication with the wireless LAN access point 180 is poor, the electronic cassette 12 cannot communicate with the console 18.

Thus, at the electronic cassette 12 relating to the present exemplary embodiment, in a case in which the settings are set to carry out communication in the ad hoc mode as the communication mode, wireless communication in the ad hoc mode is carried out. In a case in which the settings are set to carry out communication in the infrastructure mode as the communication mode, wireless communication with the console 18 in the infrastructure mode is attempted, and, if communication is not possible, wireless communication is carried out in the ad hoc mode.

Figure 12:
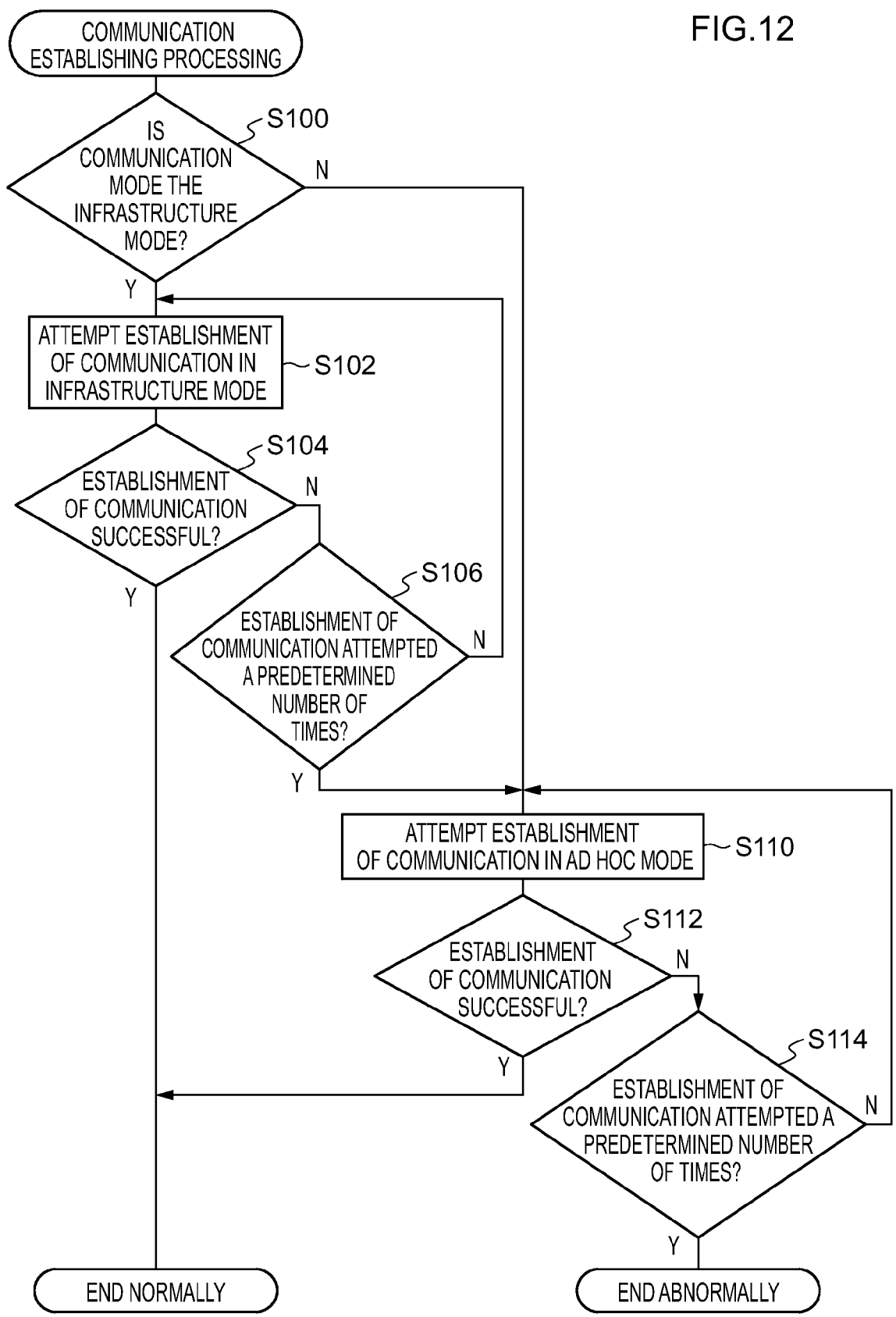
FIG. 12 is a flowchart showing the flow of communication establishing processing relating to the exemplary embodiment.

A flowchart showing the flow of communication establishing processing, that is executed by the wireless communication section 94 of the electronic cassette 12 relating to the present exemplary embodiment at the time of carrying out communication with the console 18, is shown in FIG. 12.

In step S100, it is judged whether or not the communication mode that is set is the infrastructure mode. If this judgment is affirmative, the routine moves on to step S102, whereas if the judgment is negative, the routine moves on to step S110.

In step S102, establishment of communication with the console 18 in the infrastructure mode is attempted.

In next step S104, it is judged whether or not communication with the console 18 can be established. If this judgment is affirmative, the communication establishing processing ends normally, whereas if the judgment is negative, the routine moves on to step S106.

In subsequent step S106, it is judged whether or not establishment of communication in the infrastructure mode has been attempted a predetermined number of times. If this judgment is affirmative, the routine moves on to step S110, whereas if the judgment is negative, the routine moves again to step S102 and establishment of communication is attempted.

In step S110, it is considered that the set communication mode is the ad hoc mode, and establishment of communication with the console 18 in the ad hoc mode is attempted.

In next step S112, it is judged whether or not communication with the console 18 can be established. If this judgment is affirmative, the communication establishing processing ends normally. If the judgment is negative, the routine moves on to step S114.

In next step S114, it is judged whether or not establishment of communication in the ad hoc mode has been attempted a predetermined number of times. If this judgment is affirmative, it is considered that there is a non-connectable state in which communication with the console 18 cannot be established, and the communication establishing processing ends abnormally. If the judgment is negative, the routine moves on to step S110 again, and establishment of communication is attempted.

If the communication establishing processing ends normally, the cassette control section 92 carries out communication with the console 18. If the communication establishing processing ends abnormally, the cassette control section 92 provides notification that there is a state in which communication cannot be established by, for example, causing the display portion 42A to flash in a predetermined pattern.

Due thereto, at the electronic cassette 12, even in a case in which the state of communication is poor at the time when the communication mode is the infrastructure mode and communication is carried out via the wireless LAN access point 180, wireless communication with the console 18 that is the object of communication can be established.

As described above, in accordance with the present exemplary embodiment, at the electronic cassette 12, wireless communication from the wireless communication section 94 is possible selectively in either of an ad hoc mode, in which devices communicate directly with one another, or an infrastructure mode, in which devices communicate with one another via another wireless device. In a case in which the electronic cassette 12 receives switching instruction information that instructs the switching of the communication mode from an external device, the wireless communication section 94 is controlled by the cassette control section 92 to carry out wireless communication in the communication mode expressed by the received switching instruction information. Therefore, by transmitting the switching instruction information and switching the communication mode appropriately to the infrastructure mode or the ad hoc mode, the electronic cassette 12 can be prevented from being connected to an unintended network.

Further, in accordance with the present exemplary embodiment, in a case in which communication in the ad hoc mode is designated, wireless communication is carried out in the ad hoc mode. In a case in which communication in the infrastructure mode is designated, wireless communication in the infrastructure mode is attempted with the console 18 that is the object of communication. If communication is not possible, wireless communication in the ad hoc mode is carried out. Due thereto, even in a case in which the state of communication is poor at the time when the communication mode is the infrastructure mode and communication is carried out via the wireless LAN access point 180, wireless communication with the control device that is the object of communication can be established.

In accordance with the present exemplary embodiment, the console 18 stores, in the HDD 110 and for each of the consoles 18, communication setting information that expresses the communication mode in which communication with each console 18 is carried out. Designation of the console 18 that is to be the object of communication is received, and on the basis of the communication setting information stored in the HDD 110, the communication mode for carrying out communication with the designated console 18 is specified, and switching instruction information that instructs switching to the specified communication mode is transmitted to the electronic cassette 12, and the communication mode of the electronic cassette 12 is switched. Due thereto, the electronic cassette 12 can be prevented from being connected to an unintended network.

The present invention has been described by using the above-described exemplary embodiment, but the technical scope of the present invention is not limited to the range described in the above exemplary embodiment. Various changes and improvements can be made to the exemplary embodiment within a range that does not deviate from the gist of the present invention, and forms to which such changes or improvements are made also are included within the technical scope of the present invention.

Further, the above exemplary embodiment does not limit the inventions relating to the claims, and it is not necessarily the case that all of the combinations of features described in the exemplary embodiment are essential to the means of the present invention for solving the problems of the prior art. Inventions of various stages are included in the above exemplary embodiment, and various inventions can be extracted by appropriately combining plural constituent features that are disclosed. Even if some of the constituent features are removed from all of the constituent features that are illustrated in the exemplary embodiment, such structures from which some constituent features are removed can be extracted as inventions provided that the effects of the present invention are obtained thereby.

For example, the above exemplary embodiment describes a case in which a wireless LAN is used in the wireless communication, but the present invention is not limited to the same. Any wireless communication method may be utilized provided that it includes a direct communication mode in which devices communicate directly with one another, and an indirect communication mode in which devices communicate with one another via another wireless device.

Further, the exemplary embodiment describes a case in which a console ID for identifying the console 18, environment information that expresses the image capturing environment, settings relating to the network, settings relating to wireless communication, the IP address of the console 18 that is the partner in communication, and the like for each console 18 are stored as communication setting information. In a case in which the console 18 that is the object of communication of the electronic cassette 12 is to be switched, the console 18 receives the designation of the control device that is to be the object of communication, and, from the communication setting information, specifies information relating to settings relating to the network and settings relating to wireless communication of the designated console 18, and transmits, to the electronic cassette 12, switching instruction information that includes the information relating to the settings relating to the network and the settings relating to wireless communication, and thereby switches the communication mode of the electronic cassette 12. However, the present invention is not limited to this. For example, the following structure is possible. Communication setting information such settings relating to the network, settings relating to wireless communication, the IP addresses of the consoles 18 that are to be partners in communication, and the like, that are for carrying out communication with the consoles 18 that are used in respective image capturing environments, are stored as the communicating setting information for each image capturing environment. In a case in which the console 18 that is the object of communication of the electronic cassette 12 is to be switched, the console 18 receives a designation of the environment information, and specifies, from the communication setting information, information relating to the settings relating to the network and the settings relating to wireless communication for carrying out communication with the console 18 that is used in the designated image capturing environment, and transmits switching instruction information, that includes the information relating to settings relating to the network and settings relating to wireless communication, to the electronic cassette 12, and thereby switches the communication mode of the electronic cassette 12.

Further, although the above exemplary embodiment describes a case in which the IP address, the subnet mask, the default gateway, the IP address of the DNS server and the like are stored as the communication setting information, the present invention is not limited to the same. For example, the IP address, the subnet mask, the default gateway, the IP address of the DNS server and the like may be acquired from the DHCP (Dynamic Host Configuration Protocol) server.

A case in which X-rays are used as radiation is described in the above exemplary embodiment, but the present invention is not limited to this, and may be a form that utilizes another type of radiation such as $\gamma$-rays or the like.

In addition, the structures that are described in the above exemplary embodiment are examples, and unnecessary portions may be deleted therefrom, new portions may be added thereto, and the states of connection and the like may be changed within a scope that does not deviate from the gist of the present invention.

Further, the flows of the various types of processings described in the above exemplary embodiment also are examples. Unnecessary steps thereof may be deleted therefrom, new steps may be added thereto, or the order of the processings thereof may be rearranged within a scope that does not deviate from the gist of the present invention.

In accordance with a first aspect of the present invention, there is provided a radiographic imaging device which includes: a generating unit that generates image data expressing a radiographic image formed by irradiated radiation; a first communicating unit at which wireless communication is possible selectively in either of a direct communication mode, in which devices communicate directly with one another, or an indirect communication mode, in which devices communicate with one another via another wireless device; a storing unit that stores a setting as to which of the direct communication mode or the indirect communication mode wireless communication is to be carried out in; and a control unit that, in a case in which a setting to carry out communication in the direct communication mode has been made at the storing unit, controls the first communicating unit to carry out wireless communication in the direct communication mode, and, in a case in which a setting to carry out communication in the indirect communication mode has been made at the storing unit, controls the first communicating unit to attempt wireless communication in the indirect communication mode with a control device that controls the radiographic imaging device, and, if communication is impossible, controls the first communicating unit to carry out wireless communication in the direct communication mode.

In accordance with the first aspect, image data expressing a radiographic image formed by irradiated radiation is generated by the generating means. Wireless communication by the first communicating means is possible selectively in either of a direct communication mode, in which devices communicate directly with one another, or an indirect communication mode, in which devices communicate with one another via another wireless device. Further, a setting, as to which of the direct communication mode or the indirect communication mode wireless communication is to be carried out in, is stored in the storing means.

In a case in which a setting to carry out communication in the direct communication mode has been made at the storing means, the control means controls the first communicating means to carry out wireless communication in the direct communication mode. In a case in which a setting to carry out communication in the indirect communication mode has been made at the storing means, the control means controls the first communicating means to attempt wireless communication in the indirect communication mode with a control device that controls the radiographic imaging device, and, if communication is impossible, the control means controls the first communicating means to carry out wireless communication in the direct communication mode.

In this way, in accordance with the first aspect, wireless communication is possible selectively in either a direct communication mode, in which devices communicate directly with one another, or an indirect communication mode, in which devices communicate with one another via another wireless device. In a case in which a setting to carry out communication in the direct communication mode has been made, control is carried out such that wireless communication is carried out in the direct communication mode. In a case in which a setting to carry out communication in the indirect communication mode has been made, wireless communication is attempted in the indirect communication mode with a control device that controls the radiographic imaging device. If communication is impossible, wireless communication is carried out in the direct communication mode. Therefore, even in cases in which the state of communication is poor at the time when the communication mode is the indirect communication mode and communication is carried out via another wireless device, wireless communication with the control device that is the object of communication can be established.

In accordance with a second aspect of the present invention, in the first aspect, the first communicating unit may receive, from an external device, switching instruction information that instructs switching of a communication mode, and the control unit may control the first communicating unit to carry out wireless communication in the communication mode expressed by the switching instruction information received at the first communicating unit. Due thereto, by transmitting the switching instruction information and switching the communication mode appropriately to the direct communication mode or the indirect communication mode, connection to an unintended network can be prevented.

In accordance with a third aspect of the present invention, there is provided a communication mode setting device which includes: a second communicating unit at which wireless communication with the radiographic imaging device of the second aspect is possible; a specifying unit that, in accordance with predetermined conditions, specifies a communication mode in which the radiographic imaging device is to carry out communication with a control device that is an object of communication; and a control unit that controls the second communicating unit to transmit, to the radiographic imaging device, switching instruction information that instructs switching to the communication mode specified by the specifying unit.

In accordance with the third aspect, the communication mode for carrying out communication with the control device that is the object of communication is specified. Switching instruction information, that instructs switching to the specified communication mode, is transmitted to the radiographic imaging device, and the communication mode of the radiographic imaging device is switched. Due thereto, the radiographic imaging device can be prevented from being connected to an unintended network.

In accordance with a fourth aspect of the present invention, in the third aspect, the communication mode setting device may further include: a storing unit that stores, per control device that controls the radiographic imaging device, communication mode information that expresses communication modes in which communication is carried out with the respective control devices; and a receiving unit by which the radiographic imaging device receives designation of a control device that is to be an object of communication, wherein, on the basis of the communication mode information stored in the storing unit, the specifying unit specifies a communication mode in which communication is to be carried out with the control device of the designation that the receiving unit receives. Due thereto, the appropriate communication mode for carrying out communication with the control device that is the object of communication can be set.

In accordance with a fifth aspect of the present invention, in the third aspect, the communication mode setting device may further include: a storing unit that stores, per image capturing environment in which capturing of a radiographic image is carried out, communication mode information that expresses communication modes in which communication is carried out with control devices that control the radiographic imaging device; and a receiving unit that receives designation of the image capturing environment, wherein, on the basis of the communication mode information stored in the storing unit, the specifying unit specifies a communication mode that corresponds to the image capturing environment of the designation that the receiving unit receives. Due thereto, the appropriate communication mode for carrying out communication with the control device can be set in accordance with the image capturing environment.

In accordance with the present invention, wireless communication with a control device that is an object of communication can be established, even if the state of communication is poor at the time when the communication mode is an indirect communication mode and communication is carried out via another wireless device.

Embodiments of the present invention are described above, but the present invention is not limited to the embodiments as will be clear to those skilled in the art.

What is claimed is:
1. A portable radiographic imaging device comprising:
a generating unit configured to generate image data expressing a radiographic image formed by irradiated radiation;
a first communicating unit configured such that wireless communication is possible selectively in either of a direct communication mode, in which devices communicate directly with one another, or an indirect communication mode, in which devices communicate with one another via another wireless device;

a storing unit configured to store a setting as to which of the direct communication mode or the indirect communication mode wireless communication is to be carried out in; and a control unit that, in a case in which a setting to carry out communication in the direct communication mode has been made at the storing unit, is configured to control the first communicating unit to carry out wireless communication in the direct communication mode, and, in a case in which a setting to carry out communication in the indirect communication mode has been made at the storing unit, is configured to control the first communicating unit to attempt wireless communication in the indirect communication mode with a control device that controls the radiographic imaging device, and, on condition that communication is impossible, is configured to control the first communicating unit to carry out wireless communication in the direct communication mode to communicate information which is to be communicated in the indirect communication mode if communication in the indirect communication mode were possible.

2. The portable radiographic imaging device of claim 1, wherein the first communicating unit is configured to receive, from an external device, switching instruction information that instructs switching of a communication mode, and the control unit is configured to control the first communicating unit to carry out wireless communication in the communication mode expressed by the switching instruction information received at the first communicating unit.

3. A communication mode setting device comprising:

a second communicating unit at which wireless communication with the portable radiographic imaging device of claim 2 is possible;

a specifying unit that, in accordance with predetermined conditions, is configured to specify a communication mode in which the radiographic imaging device is to carry out communication with a control device that is an object of communication; and a control unit that is configured to control the second communicating unit to transmit, to the radiographic imaging device, switching instruction information that instructs switching to the communication mode specified by the specifying unit.

4. The communication mode setting device of claim 3, further comprising:

a storing unit configured to store, per control device that controls the radiographic imaging device, communication mode information that expresses communication modes in which communication is carried out with the respective control devices; and a receiving unit by which the radiographic imaging device receives designation of a control device that is to be an object of communication, wherein, on the basis of the communication mode information stored in the storing unit, the specifying unit is configured to specify a communication mode in which communication is to be carried out with the control device of the designation that the receiving unit receives.

5. The communication mode setting device of claim 3, further comprising:

a storing unit configured to store, per image capturing environment in which capturing of a radiographic image is carried out, communication mode information that expresses communication modes in which communication is carried out with control devices that control the radiographic imaging device; and a receiving unit configured to receive designation of the image capturing environment, wherein, on the basis of the communication mode information stored in the storing unit, the specifying unit is configured to specify a communication mode that corresponds to the image capturing environment of the designation that the receiving unit receives.

6. The portable radiographic imaging device of claim 1, wherein the direct communication mode is an ad hoc mode and the indirect communication mode is an infrastructure mode via a wireless local area network (LAN) access point.

* * * * *